United States Patent
Kloetzer et al.

(10) Patent No.: US 8,026,387 B2
(45) Date of Patent: Sep. 27, 2011

(54) METHOD FOR PRODUCING ISOCYANATES

(75) Inventors: Matthias Kloetzer, Kroppen (DE);
Eckhard Stroefer, Mannheim (DE);
Heinrich-Josef Blankertz, Forst (DE)

(73) Assignee: BASF Aktiengesellschaft,
Ludwigshafen (DE)

( * ) Notice: Subject to any disclaimer, the term of this patent is extended or adjusted under 35 U.S.C. 154(b) by 369 days.

(21) Appl. No.: 12/160,433

(22) PCT Filed: Jan. 9, 2007

(86) PCT No.: PCT/EP2007/050184
§ 371 (c)(1),
(2), (4) Date: Jul. 10, 2008

(87) PCT Pub. No.: WO2007/082818
PCT Pub. Date: Jul. 26, 2007

(65) Prior Publication Data
US 2010/0274046 A1 Oct. 28, 2010

(30) Foreign Application Priority Data
Jan. 13, 2006 (EP) ..................... 06100315

(51) Int. Cl.
*C07C 249/00* (2006.01)
(52) U.S. Cl. ....................... 560/338; 560/336
(58) Field of Classification Search .......... None
See application file for complete search history.

(56) References Cited

U.S. PATENT DOCUMENTS

| | | | | |
|---|---|---|---|---|
| 2,145,242 | A * | 1/1939 | Arnold | 564/61 |
| 2005/0043563 | A1* | 2/2005 | Kohlstruk et al. | 560/345 |

FOREIGN PATENT DOCUMENTS

| | | |
|---|---|---|
| DE | 748 714 | 2/1945 |
| EP | 0 018 588 | 11/1980 |
| EP | 0 027 952 | 5/1981 |
| EP | 0 028 338 | 5/1981 |
| EP | 0 126 299 | 11/1984 |
| EP | 0 566 925 | 10/1993 |
| EP | 1 512 682 | 3/2005 |
| WO | 98 54129 | 12/1998 |

OTHER PUBLICATIONS

Houben-Weyl, Methoden der Organischen Chemie, Band VIII, s. 126-128, (1952).
U.S. Appl. No. 12/446,460, filed Apr. 21, 2009, Boehling, et al.
U.S. Appl. No. 13/125,895, filed Apr. 25, 2011, Geissler, et al.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The present invention relates to a multiple-stage process for the continuous preparation of organic, distillable polyisocyanates, preferably diisocyanates, more preferably aliphatic or cycloaliphatic diisocyanates, by reaction of the corresponding organic poly-amines with ureas to form low-molecular monomeric polyureas, and the thermal decomposition thereof.

11 Claims, 1 Drawing Sheet

METHOD FOR PRODUCING ISOCYANATES

The subject matter of the invention is a multiple-stage process for the continuous preparation of organic, distillable polyisocyanates, preferably diisocyanates, more preferably aliphatic or cycloaliphatic diisocyanates, by reaction of the corresponding organic polyamines with ureas to form low molecular weight monomeric polyureas, and the thermal decomposition thereof.

The commercial processes for preparing organic polyisocyanates, such as aromatic, aliphatic, and cycloaliphatic polyisocyanates, are based on the phosgenation of the corresponding organic polyamines to polycarbamoyl chlorides and the thermal decomposition of said polycarbamoyl chlorides to form polyisocyanates and hydrochloric acid. In addition to the serious environmental, disposal, and safety issues involved with the use of phosgene, these processes are encumbered by other major disadvantages. Due to the high alkalinity of the starting polyamines, the preparation of aliphatic or cycloaliphatic polyisocyanates results in only moderate space-time yields. Furthermore, another disadvantage is the formation of undesirable by-products which, even in trace concentrations, can lead to strong discoloration of the polyisocyanates. In the preparation of hexamethylene 1,6-diisocyanate (HDI), for example, several by-products are produced, of which the most important, 6-chlorohexyl isocyanate, has in addition the disadvantage that it can only be removed from the HDI by a distillation process that requires considerable effort.

The problems with this method are, in particular, the high conversion rate of chlorine to hydrochloric acid via phosgene and carbamoyl chloride, the toxicity of phosgene and the corrosiveness of the reaction mixture, as well as the lability of the solvents usually used and the formation of halogen-containing residues.

Although the thermal decomposition of (cyclo)aliphatic and, in particular, aromatic mono- and di-urethanes to the corresponding isocyanates and alcohol has been known for a long time, it is the undesirable side reactions in particular and above all the tendency of the reaction mixtures to form deposits, resins, and blockages in reactors and processing equipment that have a sustained negative impact on the cost-effectiveness of the processes.

In the past decades, therefore, there have been considerable efforts to overcome these disadvantages of the process via a more simple and improved process. Thus primary aliphatic and/or cycloaliphatic di- and/or poly-amines have been caused to react with O-alkyl carbamates in the presence of alcohols at temperatures of from 160 to 300° C., with and without catalysts, in order to produce aliphatic and/or cycloaliphatic di- and/or poly-urethanes, as disclosed in EP 18588 A1 as well as EP 28338 A2. The resulting di- and/or poly-urethanes can then be converted into the corresponding isocyanates. At the same time, the ammonia generated during the reaction of the amines can be removed.

Other publications deal with the partial substitution of urea and/or diamines by compounds containing carbonyl groups (eg, EP 27952 or EP 126299). The phosgene-free process is described in detail, for example, in EP 566925 A2.

The disadvantage of the latter process is that the intermediately-formed polyureas must be converted in another reaction stage into the corresponding carbamates, which carbamates can then be broken down. Direct decomposition of the directly obtained polyureas is not possible, as the breakdown products, amine and isocyanate, mostly react with each other while still in the gas phase of the breakdown reactor but never later than the formation of condensate.

The thermal decomposition of ureas to prepare isocyanates is known in principle; see, for example, Houben-Weyl, Methoden der organischen Chemie, Vol. VIII, pp. 126-128, 1952. The method described therein, however, is only suitable for preparing high-boiling diphenylamine. In addition, diphenylamine must be reacted with phosgene in an upstream stage to form the corresponding diphenylcarbamoyl chloride; consequently, this reaction is not phosgene-free.

According to the process of German Patent 748 714, however, only trisubstituted ureas comprising not more than two aryl groups are suitable for thermolysis. The disadvantage of this process is that both of the amide groups of these ureas must correspond to two amines having considerably different boiling points, whilst only low-boiling isocyanates can be prevented from recombination by distillation.

Consequently, the urea breakdown processes known in the prior art can only be performed with special substituted ureas.

Therefore, the processes known in the prior art are suitable solely for the preparation of monoisocyanates but not for the conversion of di- or poly-amines.

Figure 1:
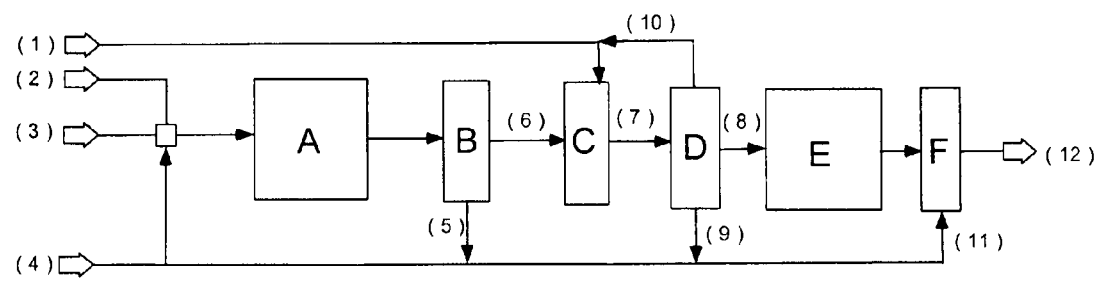
FIG. 1 shows a flow diagram for the process described in Example 1 of the specification.

It is an object of the present invention to provide a process for the preparation of organic polyisocyanates by decomposition of the corresponding polyureas.

This object is achieved by means of a process for the preparation of isocyanates by reaction of at least one di- or poly-amine with urea to form the corresponding di- or poly-urea followed by breakdown of the resulting di- or poly-ureas to produce the corresponding isocyanates.

The subject matter of the invention is a multiple-stage process for the continuous preparation of organic di- or poly-isocyanates by reaction of the corresponding primary organic di- or poly-amines with urea to form the corresponding di- or poly-ureas and the thermal decomposition thereof, wherein a) at least one organic di- or poly-amine is caused to react with urea in the presence of, or preferably in the absence of, at least one catalyst and in the absence of an alcohol to form the corresponding di- or poly-ureas, b) the resultant ammonia is removed, c) excess urea and, if appropriate, other minor constituents are separated off from the effluent from a) or b), d) the reaction mixture comprising di- or poly-ureas freed from the urea and, if appropriate, other minor constituents coming from c) is fed, at least in part, to a thermal decomposition stage, in which the reaction mixture is decomposed in a disintegrator to form the corresponding di- or poly-isocyanate and ammonia, e) the crude isocyanate obtained in (d) is purified in at least one distillation stage and the resulting distillation residues are at least in part returned to the decomposition stage (d) and/or converted to di- or poly-urea and/or amine with ammonia and/or water and recycled to the reaction unit (a) and/or (b).

The process of the invention shows higher yields than processes known in the prior art.

From a purely theoretical standpoint, the process of the invention can be schematically summarized by the following equation:

Amines of the formula $R(NH_2)_n$ are suitable as di- and poly-amines $R—(NH_2)_n$, referred to herein simply as amine, wherein R represents an n-valent, preferably divalent organic radical, such as an optionally substituted, eg alkyl-substituted, aromatic radical or preferably a linear or branch-chained aliphatic radical or an optionally substituted cycloaliphatic radical.

The index n represents a positive integer of 2 or more, preferably 2, 3, or 4, more preferably 2 or 3 and even more preferably 2.

2,4- and 2,6-toluenediamine, 4,4'-, 2,4'- and 2,2'-diaminodiphenylmethanes and the corresponding isomer mixtures are examples of suitable aromatic polyamines.

Examples of suitable aliphatic or cycloaliphatic polyamines are butanediamine-1,4,2-ethylbutanediamine-1,4, octanediamine-1,8, decanediamine-1,10, dodecanediamine-1,12, cyclohexanediamine-1,4,2-methyl- and 4-methylcyclohexanediamine-1,3,1,3- and 1,4-diaminomethylcyclohexane, 4,4'-di(aminocyclohexyl)methane, 3,8- or 4,9-bis(aminomethyl)tricyclo[$5.2.1.0^{2.6}$] decane isomer mixtures. Preference is given to the use of 2-methylpentanediamine-1,5,2,2,4- or 2,4,4-trimethylhexanediamine-1,6, and especially hexanediamine-1,6 and 3-aminomethyl-3,5,5-trimethylcyclohexylamine.

Unsubstituted urea $H_2N—(CO)—NH_2$ is designated as urea in this text. The biuret fraction in urea plays a subordinate role in the invention and can comprise preferably not more than 1% by weight, more preferably not more than 0.5% by weight and even more preferably not more than 0.3% by weight.

The individual stages of the process are described below:
a) Reaction of the amine with urea To produce the di- or poly-ureas in the reaction stage (a), the corresponding amines are advantageously caused to react with urea in an amine to urea molar ratio of from 1:50 to 1:2, preferably from 1:30 to 1:3, more preferably from 1:20 to 1:5, and even more preferably from 1:15 to 1:8, at temperatures of from 50 to 300° C. and especially from 180 to 220° C. under a pressure of from 0.1 bar to 30 bar, preferably from 1 bar to 20 bar. These reaction conditions result in average reaction times ranging from fractions of a second to minutes, preferably from 0.1 sec to 5 min and more preferably from 0.5 sec to 3 min.

The reaction in reaction stage (a) can also take place in the presence of catalysts. Said catalysts are advantageously used in quantities of from 0.001% to 20% by weight, preferably from 0.002% to 5% by weight and more preferably from 0.005% to 0.1% by weight, based on the weight of the amine.

Suitable catalysts are inorganic or organic compounds comprising one or more cations, preferably a cation from the metals of groups IA, IB, IIA, IIB, IIIB, IVA, IVB, VA, VB, VIB, VIIB, VIIIB of the Periodic Table, as defined in the Handbook of Chemistry and Physics, 14th Edition, published by the Chemical Rubber Publishing Co., 23 Superior Ave. N.E., Cleveland, Ohio. The cations of the following metals are cited as examples: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, and cobalt.

Furthermore, the catalyst can comprise at least one anion, for example, halogenides such as chlorides and bromides, sulfates, phosphates, nitrates, borates, alcoholates, phenolates, sulfonates, oxides, hydrated oxides, hydroxides, carboxylates, chelates, carbonates, and thio- or dithio-carbamates.

The catalysts can also be used in their hydrate or ammoniate forms with no significant detectable disadvantages.

The following compounds are listed as examples of typical catalysts: lithium methanolate, lithium propanolate, lithium butanolate, sodium methanolate, potassium tert-butanolate, magnesium methanolate, calcium methanolate, tin(II) chloride, tin(IV) chloride, lead acetate, lead phosphate, antimony (III) chloride, antimony(V) chloride, aluminum acetylacetonate, aluminum isobutylate, aluminum trichloride, bismuth (III) chloride, copper(II) acetate, copper(II) sulfate, copper (II) nitrate, bis(triphenylphosphinoxido)-copper(II) chloride, copper molybdate, silver acetate, gold acetate, zinc oxide, zinc chloride, zinc acetate, zinc acetonylacetate, zinc octoate, zinc oxalate, zinc hexylate, zinc benzoate, zinc undecylenate, cerium(IV) oxide, uranyl acetate, titanium tetrabutanolate, titanium tetrachloride, titanium tetraphenolate, titanium naphthenate, vanadium(III) chloride, vanadium acetylacetonate, chromium(III) chloride, molybdenum(VI) oxide, molybdenum acetylacetonate, tungsten(VI) oxide, manganese(II) chloride, manganese(II) acetate, manganese(III) acetate, iron(II) acetate, iron(III) acetate, iron phosphate, iron oxalate, iron(III) chloride, iron(III) bromide, cobalt acetate, cobalt chloride, cobalt sulfate, cobalt naphthenate, nickel chloride, nickel acetate and nickel naphthenate, and mixtures thereof.

The following compounds are listed as examples of preferred catalysts: lithium butanolate, aluminum acetylacetonate, zinc acetylacetonate, titanium tetrabutanolate, and zirconium tetrabutylate.

To carry out the reaction, amine and urea, and optionally solvent and catalyst, are preferably introduced into a mixing device and thoroughly mixed with each other.

Preference is given to a mixing circuit, an agitator, a mixing pump or a jet mixing device, for example, coaxial mixing nozzles, Y or T mixers or a vortex impinging jet mixer configuration, for use as a mixing device, which is preferably a mixing circuit, an agitator, a mixing pump or a jet mixing device.

The urea is preferably metered in liquid form into the reaction or the mixing device. However, the urea may be less preferably introduced into the reaction as a solid urea paste in a liquid amine or in the form of a solution in a suitable solvent, preferably water.

Stirred vessels, cascades of stirred vessels or tubular reactors, as well as reaction mixing pumps, are examples of reactors that can be used for the reaction.

The reaction is preferably carried out under conditions in which, in addition to the liquid reaction phase, another, gaseous phase can develop from the ammonia formed during the reaction. It is less preferable to maintain the reaction as a monophase reaction, for example, by applying pressure.

It is preferable for tubular reactors to be prevented from backmixing as far as possible. This is achieved, for example, by adjusting the diameter-length ratio of the tubular reactor, or by the use of internal fittings such as perforated or slotted trays, or static mixers. It is preferable to eliminate backmixing by adjusting the diameter-length ratio of the tubular reactor.

Tubes such as those in which the previously described average residence time of the reaction medium is achieved and in which a turbulent stream (Reynolds numbers greater than 2300) is at the same time achieved are suitable as tubular reactors.

The Bodenstein number of the tubular reactor should be greater than 5, preferably greater than 6, more preferably greater than 10, even more preferably from 10 to 600 and most preferably from 10 to 100.

The tubular reactor can assume any spatial orientation. It is preferably designed as a perpendicular tubular reactor, particular preference being given to one having a continuous upward stream.

The tubular reactor may be designed for isothermal operation or, preferably, for operation with heat control. Temperature control can be achieved by jacket heating or via internal tubes or plates. Heating is preferably achieved via the jacket.

Obviously the tubular reactor may also consist of a plurality of in-line connected tube sections, as long as the prevention of backmixing is assured. If needed, optional phase separators for separating the liquid and gaseous phases can be provided along the length of the tubular reactor, for example between such tube sections, in which ammonia generated during the reaction can be removed so that the balance of the reaction is shifted.

According to the invention, a plurality of tubular reactors may also be connected in parallel in order to increase the production capacity.

If appropriate, additional urea, or preferably amine, can be metered into the tubular reactor, as described above, at one or more points, for example at the beginning and in the middle of the tubular reactor.

In order to maintain the gas load at a low level for the next stage, the effluent from the tubular reactor can be fed to a phase separator, and the liquid phase removed from said phase separator can then be fed to said next stage, in a preferred embodiment.

Such a phase separator is a tank in which the phase separation between gaseous and liquid phases is achieved via the settling of the two-phase stream leaving the continuous-flow-tubular reactor.

The phase separator may be designed for isothermal operation or preferably for heated operation, in order to prevent any precipitation of by-products that are not readily soluble. The heating can be effected, for example, via the jacket or via a circuit comprising an external heat exchanger. Standard insulation of the heat exchanger is adequate if an external heat exchanger is used.

The transfer of the reaction effluent from this stage to the subsequent stage can be advantageously achieved via pressure holding valves, wherein the pressure in this stage should usually be at least 0.1 bar higher than the pressure in stage b). If this is not the case, the transfer may be achieved, for example, with the aid of a pump or barometrically.

The residence time in this stage is selected so that the conversion, based on the amino groups in the amine used relative to the urea groups, is at least 95%, preferably at least 98%, more preferably at least 99% and even more preferably at least 99.5% after leaving the tubular reactor.

With complete conversion of the amines to di- or poly-urea, the effluent of the reaction mixture can be fed directly to the ammonia removal stage (b) if this has not already taken place during the reaction, or the effluent is fed to another reactor or reactor system in order to achieve complete conversion. Other tubular reactors, cascades of mixing reactors or columns with the necessary mean residence time can be used as reactors.

If the conversion, based on the amino groups in the amine used relative to the urea groups, is still not complete after leaving the tubular reactor and is less than, for example, 95%, the effluent can be caused to react once more.

In order to complete the conversion, the reaction mixture can be allowed to react in another tubular reactor or in a backmixed reactor, preferably until a 98% or greater conversion is achieved.

A backmixed reactor system in this sense implies that the Bodenstein number of the reactor system is less than 5 and preferably less than 4.

b) Ammonia Removal

It has been shown that it is advantageous to remove the generated ammonia from the reaction mixture immediately. The device used for this purpose, for example a distillation column, is operated at temperatures of from 50 to 180° C. On the one hand the temperature is adjusted substantially according to the melting point of the reaction product generated in the reaction stage (a), and on the other hand according to the boiling point of the solvent used.

It is advantageous to use columns for the removal of the ammonia, which is preferably removed via distillation. In general, the removal takes place in a pressure range of from 0.005 bar to 20 bar and preferably from 0.04 bar to 15 bar. The necessary temperatures are in the range of, say, from 50 to 180° C. and preferably from 80 to 160° C.

Said distillation unit has a construction known per se and comprises the usual internal fittings. In principle, all standard internal fittings can be used as column internal fittings, for example trays, packings and/or beds. Among the trays, preference is given to bubble-cap trays, sieve trays, valve trays, Thormann trays and/or dual flow trays, and among the beds, preference is given to those comprising rings, coils, saddles, Raschig rings, Intos rings, or Pall rings, barrel saddles or Intalox saddles, Top-Pak, etc. or braids. Preference is given to using trays and particular preference to bubble-cap trays.

The distillation column preferably comprises up to 20 theoretical trays.

It has been shown to be advantageous to remove the generated ammonia immediately from the reaction mixture, preferably during the reaction in stage a), in order to avoid a deposit of ammonium carbaminate, which is formed in minute quantities from ammonia and carbon dioxide by the breakdown of urea.

In particularly preferred embodiment, a so-called flash is used for the removal of ammonia by distillation. This apparatus may be a tank or a combination of tanks and columns, preferably a column, wherein ammonia can be withdrawn from the head and the di- or poly-urea can be withdrawn from the bottoms. In the head of the column there may also be other substances with lower boiling points than the di- or poly-urea, in addition to the ammonia. The removal takes place in a pressure range of from 0.001 bar to 1 bar and preferably from 0.02 bar to 0.5 bar and at a temperature of from 50 to 180° C. and preferably from 80 to 150° C.

If necessary, the removal can be enhanced by passing through a gas that is inert under the removal conditions, preference being given to nitrogen.

In order to retain liquid components entrained with the stream, said components can be removed from the gas stream via downstream dephlegmators or droplet removers. It is also possible, however, to place one or more partial condensers in the diverted gas stream, in which condensers the fluid entrained in the stream is condensed.

c) Removal of the Excess Urea

The urea used is dissolved by a suitable process and then removed from the reaction mixture (a) and/or (b) obtained during the continuous operation in the first reaction stage.

All substances in which urea is readily soluble, ie, has a solubility greater than from 200 g of urea per liter at the respective dissolution temperature, can be used as solvents.

Alcohols and water are examples of solvents.

Methanol, ethanol, n-propanol, isopropanol, n-butanol, sec-butanol and isobutanol are examples of alcohols. It is necessary to ensure that the temperature used in the stage involving the removal of the urea from the di- and poly-ureas is sufficiently low to prevent the alcohol from reacting with the functional groups.

According to the invention, preference is given to dissolution in water.

Surprisingly, the diureas formed in the reaction stage (a) dissolve very poorly, ie, less than 3 g/l, in water at temperatures of from 0 to 60° C., especially from 10 to 20° C., so that in the separation of the reaction products following this stage of the process, the solid substance (di- or poly-ureas) and the preferably aqueous urea solution can be removed without major yield losses.

This can be achieved via any solid-liquid separation, for example by filtration or centrifugation. Fractional crystallization might also be conceivable.

The urea is recovered from the preferably aqueous urea solution in a suitable apparatus and recycled to the reaction stage. To achieve this end, preference is given to rectification or particular preference is given to one-step distillation. Suitable apparatus for this purpose includes flash evaporators, falling-film evaporators, thin-film evaporators and/or short path evaporators, to which a short column can be optionally attached. The urea is then preferably recovered as molten material and recycled.

If water has already been used as the solvent in the first stage, the remaining solution can be recycled directly to stage a), optionally after partial removal of the solvent.

In order to improve the demixing of the urea and di- or poly-urea mixture, it may also be advantageous to add an organic co-solvent that is not miscible with the urea solution and with which the mixture can be separated into an aqueous phase and an organic phase. Usually, the di- and poly-ureas are either insoluble or poorly soluble in standard organic solvents under the conditions of the reaction.

If there is another solvent present, it is preferred to carry out phase separation. The organic solvent can also then be removed from the di- or poly-ureas, preferably by distillation, and recycled to stage (c).

In a preferred embodiment, the di- or poly-ureas, prior to being fed into stage d), still have a water content and/or an alcohol content, particularly a water content of not more than 10% by weight, preferably not more than 7.5% by weight, more preferably not more than 5% by weight and most preferably not more than 3% by weight. This is particularly preferable in the case of diureas which are derived from 3-aminomethyl-3,5,5-trimethylcyclohexylamine. Such a residual solvent content maintains the fluidity of the reaction mixture and thus improves the flow.

d) Urea Breakdown

The di- or poly-urea removed from the reaction mixture undergoes thermal decomposition in a suitable apparatus.

The reaction mixture comprising di- or poly-ureas obtained from the reaction stage (c) undergoes continuous thermal decomposition in a suitable device, preferably solventfree or in the presence of only minimal volumes of water and/or alcohol, in a liquid phase in the presence of or preferably in the absence of catalysts at temperatures of from 150 to 450° C., preferably from 200 to 400° C. and under a reduced pressure of from 0.01 bar to 0.6 bar and preferably in the range of from 0.02 bar to 0.1 bar.

Preference is given to selecting residence times ranging from 0.01 sec to 20 sec.

Depending on the polyurea used, there is considerable freedom of choice when adjusting the rate of conversion of polyurea to polyisocyanate, preferably of diurea to diisocyanate, in the thermal decomposition device. This conversion rate is advantageously in the range of from 10% to 99% by weight, preferably 40% to 98% by weight and more preferably from 70% to 95% by weight of the polyurea feed.

The unconverted fraction of the reaction mixture comprising unconverted polyureas, oligourea-polyureas, high-boiling oligomers and other reprocessable and non-processable by-products is removed, continuously discharged from the breakdown device (stream $d_H$) and recycled, either directly or, if appropriate, after reaction with ammonia or water, to the reaction stage (a).

The aforementioned inorganic and organic compounds that catalyze urea formation are examples of catalysts used for the chemical decomposition of the polyureas.

Dibutyltin dilaurate, iron(III) acetylacetonate, cobalt(II) acetylacetonate, zinc acetylacetonate, zirconium tetra-n-butanolate and tin(II) dioctoate have proven to be especially effective and therefore preference is given to the use of same.

Examples of suitable breakdown devices are cylindrical breakdown reactors such as tubular ovens or preferably evaporators, for example thin-film evaporators or bulk evaporators, such as Robert evaporators, Herbert evaporators, Caddle-type evaporators, plate reactors, and preferably glow-plug evaporators.

In a preferred embodiment of the present invention, the decomposition is carried out in a fluidized-bed reactor.

Standard materials in the form of, for example, powders or pellets, such as balls, rings, cylinders or tablets, with a preferred grain size of from 0.01 mm to 10 mm and more preferably from 50 µm to 500 µm, are used as fluidizing media.

The fluidized bed facilities generally comprise, for example, a cylindrical fluidized bed tank having an inside diameter-length (height) ratio that is generally from 1:0.5 to 1:10 and preferably from 1:1 to 1:7, having a fluidized bed, the inflow tray for the fluidizing gas, which may consist, for example, of a frit tray, a round-hole or bubble-cap tray or a CONIDUR fine hole plate, a nozzle for the feed of reactant, ie, the di- or poly-urea feed and for the discharge of product and waste gas, which can optionally take place via a filter located in the fluidized bed tank or via cyclones, if appropriate a mechanical comminuting device for the fluidized medium and, if appropriate, heating surface internal fittings. The di- or poly-ureas are injected into the fluidized bed preferably in a vaporous, dissolved, or molten form, more preferably in vaporous form.

The fluidizing gas used is preferably nitrogen, which can, if appropriate, be used in mixtures with other compounds, for example with inert substances such as helium, (cyclo)aliphatic and/or aromatic, optionally substituted hydrocarbons having a boiling point generally lower than 250° C., examples of which include decane, undecane, dodecane, tridecane, tetradecane, naphthalene, toluene, benzene, 1,2-, 1,3-, and/or 1,4-dimethylbenzene, chlorobenzene, and aliphatic and/or aromatic ketones such as cyclohexanone. The fluidizing gas is preferably fed in through the inflow tray and the di- or poly-urea to be decomposed is preferably injected into the fluidized bed tank through a side nozzle located in the bottom half of the fluidized bed.

As fluidized medium, preference is given to using carbon and/or optionally vitreous oxides comprising boron, aluminum, silicon, tin, lead, antimony, zinc, yttrium, lanthanum, titanium, zirconium, niobium, tungsten and/or iron and optionally magnesium, calcium and/or phosphorus. As fluidized medium, particular preference is given to using silicon oxides, carbon and/or a steatite, with particular preference being given to silicon dioxide or a steatite of the general chemical formula $Mg_3[SiO_{10}(OH)_2]$. The advantage of using steatite is that polymer deposits formed in the fluidized bed or on the fluidized bed tank during the process can be removed by burning.

Preference can thus be given to a method for breaking down di- or poly-ureas wherein di- or poly-urea and fluidizing gas are continuously fed, separately or together, into a fluidized bed preferably comprising silicon dioxide or steatite as fluidized medium, and wherein isocyanate and ammonia are continuously removed and cooled (see below).

The resultant breakdown products are rapidly cooled. Heat exchangers or columns are apparatus suitable for this purpose. Cooling must take place quickly, otherwise back reactions and thus blockages may result.

In order to reduce the concentration of the breakdown products, a solvent may be used or, in the event that the decomposition takes place in a fluidized bed, the fluidizing gas can be used to this end. The ammonia present in the breakdown gases is removed from the reaction mixture, in which the corresponding isocyanates are already present in high concentrations, by flashing or distillation.

Cooling of the breakdown products may take place either indirectly, for example in condensers such as shell-and-tube condensers or plate condensers, or preferably directly. A preferred possibility for direct condensation according to the invention is quenching; in other words, cooling of the breakdown products via direct contact with a cooling medium.

All devices known in the prior art as quenching or prequenching devices, such as spray coolers, Venturi washers, bubble columns or other apparatus with sprinkled surfaces may be used to this end, preference being given to using Venturi washers or spray coolers.

According to the invention, preference is given to an average cooling time of less than 10 seconds, preferably less than 5 seconds, more preferably less than 3 seconds, even more preferably less than 2 seconds, very preferably less than 1 second and most preferably less than 0.5 second. Cooling times of less than 0.3 sec, less than 0.2 sec, or even only 0.1 sec are also conceivable.

The cooling time is defined as the interval between the point in time of the origin of the breakdown product mixture and the point in time at which the breakdown product mixture completes 90% of the temperature change to the adiabatic end temperature. Intervals of this order of magnitude can virtually rule out any isocyanate losses due to side reactions or continuing reactions. The adiabatic end temperature is the temperature that results when the reaction mixture and the quenching fluid are mixed in the respective volume streams at their starting temperatures under adiabatic conditions.

Preferably at least one quenching medium, preferably a liquid quenching medium with a temperature lower than that of the product gas mixture, is brought into contact with said product gas mixture in a suitable manner. The quenching medium is preferably injected into the quenching zone to form a curtain of quenching medium through which the product gas mixture is fed.

The liquid droplets of the quenching medium are produced via one-phase or two-phase atomizers, preferably one-phase atomizers, and said droplets preferably have a Sauter diameter $d_{23}$ of from 5 μm to 5000 μm, more preferably from 5 μm to 500 μm and most preferably from 5 μm to 250 μm. The Sauter diameter $d_{23}$ describes the ratio of droplet volume to droplet surface area relative to a constant factor (K. Schwister: Taschenbuch der Verfahrenstechnik, Fachbuchverlag Leipzig, Carl Hanser Verlag 2003) and is thus the fundamental parameter of the droplet size distribution generated for the quenching process.

Depending on the embodiment, the atomizers produce a spray cone angle of from 10° to 140°, preferably from 10° to 120° and more preferably from 10° to 100°.

Usually, the velocity at which the droplets leave the nozzle is at least 5 m/s, preferably at least 10 m/s and more preferably at least 25 m/s. Usually, the velocity is not greater than 200 m/s, preferably not greater than 100 m/s and more preferably not greater than 75 m/s.

The number of atomizers is not limited and may comprise, for example, from 1 to 10, preferably from 1 to 6, more preferably from 1 to 4, even more preferably from 1 to 3 and most preferably from 1 to 2 per inlet for the product gas mixture.

The effluent is preferably transferred from one breakdown zone to the quenching zone; however, the effluents from a plurality of breakdown zones may also be fed through one or more inlets into one quenching zone.

It is also possible to divide the effluent from one breakdown zone and feed it into one or more quenching zones via a plurality of inlets.

The di- or poly-ureas should preferably be readily soluble, and the ammonia should be largely insoluble in the liquid injected through the atomizers. Preference is given to using organic solvents. Aliphatic or aromatic solvents in particular are used, which solvents can be substituted by halogen atoms. Examples of such liquids are toluene, benzene, nitrobenzene, anisole, chlorobenzene, dichlorobenzene (ortho, para), trichlorobenzene, xylene, hexane, diethyl isophthalate (DEIP), mixtures comprising aromatic and/or aliphatic hydrocarbons that can comprise a boiling range of from 60 to 200° C., as well as tetrahydrofuran (THF), dimethylformamide (DMF), and mixtures thereof.

The temperature of the injected liquid preferably ranges from 0 to 200° C., more preferably from 50 to 150° C. and most preferably from 70 to 120° C., so that the desired cooling and condensation of the di- or poly-urea is achieved with the amount of liquid injected. This substantially causes the reaction to stop.

The velocity of the product gas in the quenching zone is preferably greater than 1 m/s, more preferably greater than 10 m/s and most preferably greater than 20 m/s.

The mass ratio of injected liquid volume to the volume of the gaseous reaction mixture is preferably from 100:1 to 1:10, more preferably from 50:1 to 1:5 and most preferably from 10:1 to 1:2.

The separation of the breakdown products and the quenching medium can take place in a column in which the isocyanate is generally withdrawn from the side $(d_M)$ and the ammonia $(d_L)$ from the top. However, preference is given to a two-fold partial condensation in heat exchangers, wherein predominantly isocyanate is partially condensed in the first heat exchanger and predominantly quenching medium is partially condensed in the second heat exchanger, according in each case to the degree of heat dissipation and the boiling temperature of the solvent. Ammonia is then removed along with solvent fractions as a gas stream.

e) Isocyanate Purification

The crude isocyanate mixture is freed from back reaction products, by-products and any remaining solvent in a subsequent distillation stage. The by-products are preferably recycled to the thermal decomposition. A portion thereof can also be discarded. The breakdown products formed in the thermal decomposition, which are composed primarily of ammonia, polyisocyanate, preferably diisocyanate, and partially converted polyureas, are advantageously separated in stage (e) into low boilers and, in particular, ammonia $(e_L)$ and a crude polyisocyanate mixture $(e_M)$ with a polyisocyanate content of from 85% to 99% by weight and preferably from 95% to 99% by weight with the aid of one or more distillation columns, preferably by rectification at temperatures of from 100 to 220° C. and more preferably from 120 to 170° C. and under a pressure of from 1 mbar to 200 mbar and preferably from 5 mbar to 50 mbar. The higher boiling by-products ($e_H$) precipitating out in the distillative separation, and especially the unconverted and partially converted polyureas, are preferably fed into the breakdown device (d) and/or to recovery stage (f).

Low boiling streams of the individual stages are designated herein by the index "L" and the high boiling streams are designated by the index "H" and the medium boiling streams by "M".

The crude polyisocyanate mixture ($e_M$) preferably obtained via rectification can be purified by distillation at a temperature of from 100 to 180° C. and under a pressure of from 1 mbar to 50 mbar, wherein the individual fractions are recycled or isolated as refined product. As previously described, the head fraction in the preferred refining distillation, which is preferably composed of polyisocyanate, in particular diisocyanate, is recycled, optionally after the reaction of the free isocyanate groups with ammonia, in the reaction stage (a) or the ammonia removal stage (b); the side fraction, which is composed of refined polyisocyanate, especially diisocyanate, preferably with a purity of at least 98% by weight, especially greater than 99% by weight, is withdrawn and fed to storage containers, and the bottom fraction, which comprises the partially converted polyureas and polyisocyanates as main components, is preferably recycled to the breakdown device for thermal decomposition.

According to other process variants, the bottom fraction ($e_H$) can be recycled to the distillation column (c) for separation from the crude polyisocyanate and the ammonia, or recycled to the reaction stage (a), ie, the polyurea formation stage. It is also possible to separate the bottom fraction into 2 or 3 product streams, which product streams are preferably recycled to the polyurea formation stage (a) and the breakdown device (d) as well as, if appropriate, to the distillation column (e) or the recovery stage (f).

f) Recovery

The conversion of the reaction effluent ($d_H$) from d) and/or the distillation residues ($e_H$) from (e) can optionally be recycled to the process. The isocyanate groups and/or ureas or other reactive components present in this mixture are reacted using with ammonia to produce optionally lower molecular weight ureas. It is also possible to conduct these reactions in separate reactors such as mixing reactors or continuous-tubular-flow reactors or else in (a). Temperatures of from 20 to 250° C. and preferably from 50 to 220° C. are required for the ammonolysis of the residues. The average residence times lie within a range of a few seconds to several hours.

To this end, the streams ($d_H$) and/or ($e_H$) and, if appropriate, part of the stream ($d_H$), for example, can be fed in together with ammonia, the molar ratio of NCO groups or their equivalents, for example urea groups, to ammonia being not more than 1:100, preferably not more than 1:20, and more preferably not more than 1:10.

Preference is given to carrying out the reaction with supercritical ammonia.

The ammonia can be, for example, the low boiling stream ($c_L$) from stage (c) and/or the ammonia-containing stream ($d_L$) from the urea breakdown stage (d) and/or fresh ammonia.

The reaction mixture is converted in the presence or absence of catalysts within from 1 min to 150 min and preferably within from 3 min to 60 min at temperatures of from 20 to 200° C. and preferably from 50 to 170° C. under a pressure of from 0.5 bar to 20 bar and preferably from 1 bar to 15 bar.

The reaction can take place in a continuous cascade of tanks or in a tubular reactor, preferably in a single phase.

In principle, all compounds that catalyze the reaction of NCO— with ammonia can be used as catalysts. Tin octoate, dibutyltin dilaurate, tin chloride, zinc dichloride, tin(II) dioctoate and triethylamine are cited as examples. Mostly, however, no catalysts are required.

The process of the invention is especially suitable for the production of aliphatic diisocyanates, such as 2-methylpentane 1,5-diisocyanate, isomers of aliphatic diisocyanates containing 6 carbon atoms in the alkylene radical and mixtures thereof and preferably hexamethylene 1,6-diisocyanate and cycloaliphatic diisocyanates, especially 3-isocyanatomethyl-3,5,5-trimethylcyclohexyl isocyanate by an economical method.

The polyisocyanates produced are especially suitable for the production of synthetic materials comprising urethane groups, isocyanurate groups, amide groups and/or urea groups by the polyisocyanate polyaddition process. They are also used in the production of polyisocyanate mixtures modified with urethane groups, biuret groups and/or isocyanurate groups. Such polyisocyanate mixtures of aliphatic or cycloaliphatic diisocyanates are used especially for the production of light-resistant polyurethane varnishes and coatings.

The following examples serve to explain the invention; however, the invention is not restricted to these examples.

Example 1

1,6-hexamethylenediamine is placed in a tank at a temperature of 90° C. A second tank is filled with toluene. A stream of 0.9 kg/h of 1,6-hexamethylenediamine ((2) in FIG. 1), 8 kg/h of toluene (4) and 6 kg/h of liquid urea (3) is fed in through a mixing nozzle by means of pumps. The streams are heated with heat transfer means so that the temperature in the nozzle is at least 130° C.

After leaving the nozzle, the reaction mixture flows through a jacket-heated tubular reactor (A). Depending on the operation mode, the temperatures in the reactor lie in the range of from 170 to 220° C. under a pressure of 13 bar. The length of the reactor is about 8 m. Nearly 100% amine conversion is achieved. The yields of 1,6-hexamethylenediurea are about 98%.

The reaction mixture from the continuous-tubular-flow reactor is then freed from most of the ammonia in a flash (B). The temperature in the flash is 110° C. under a pressure of about 1.1 bar. About half of the solvent is entrained as vapor to a condensation system. Two coolers connected in line separate the ammonia from the solvent. The toluene is collected (5) and recycled to the nozzle.

The liquid effluent (6) from (B) is fed into a mixing system (C) (150 ml stirred reactor). The temperature in said reactor is 20° C. and the pressure is approximately atmospheric pressure. An additional 1 kg/h of water (1) is metered into this mixing reactor. The effluent (7) from the mixer (C) is fed to a phase separating vessel (D). The 1,6-hexamethylenediurea that is insoluble in the organic and aqueous phases is continuously withdrawn with a pump as a bottoms suspension (8). The top phase ((9), toluene) is likewise continuously withdrawn with a pump, collected and recycled to the reaction stage (A). The water (10) is withdrawn as a middle phase. The excess urea not converted in (A) is in solution in this fraction.

The aqueous stream from the phase separator (D) is gently vaporized at from about 60 to 80° C. and 300 hPa, and the vapor is condensed and recycled to the mixer (C). The residual urea is fed to the reactor system (A) (this step is not shown in FIG. 1).

The 1,6-hexamethylenediurea (8) drawn from the phase separating vessel (D) is fed directly into a fluidized-bed reactor (E). The temperature of said reactor is 380° C. Sand (3.5 kg) was used as the fluidized medium. The diameter of said reactor is 10 cm. The vapors leaving the reactor were rapidly cooled in a flash (F) with toluene (11) in order to separate the resultant 1,6-hexamethylene diisocyanate (HDI, (12)) rapidly from the ammonia. The yield of HDI in this process stage was 89%. The ureas formed during the separation were recycled to the phase separating vessel (D) (this step is not shown in FIG. 1).

Example 2

Figure 2:
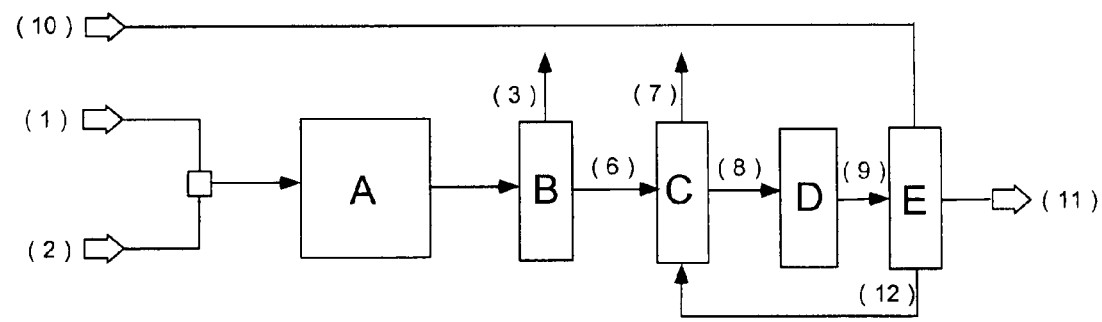
FIG. 2 shows a flow diagram for the process described in Example 2 of the specification.

Isophoronediamine (3-aminomethyl-3,5,5-trimethylcyclohexylamine) is placed in a tank at a temperature of 90° C. A second tank is filled with water and solid urea is dissolved therein to give a concentration of 400 g/l. A stream of 0.9 kg/h of isophoronediamine ((1) in FIG. 2) and 1.58 l/h of water/urea mixture (2) are pumped in through a mixing nozzle. The streams are preheated with heat transfer means so that the temperature in the nozzle is at least 130° C.

After leaving the nozzle, the reaction mixture flows through a jacket-heated tubular reactor (A). Depending on the operation mode, the temperatures in the reactor lie in the range of from 170 to 220° C. under a pressure of 13 bar. The length of the reactor is about 8 m. Nearly 100% amine conversion is achieved. The yields of isophoronediurea are about 98%.

The reaction mixture from the continuous-tubular-flow reactor is then freed from most of the ammonia and water in a flash (B). The temperature in the flash is 110° C. under a pressure of about 1.1 bar. About half of the water is entrained as steam to a condensation system. Two coolers connected in line separate the ammonia from the solvent. The water is collected (3) and recycled to the initial batch tank.

The liquid effluent (6) from (B) is fed to a thin-film evaporator (C). At a pressure of 1 bar, most of the residual water is separated as a vapor phase (7) and the liquid diurea bottoms effluent is withdrawn by a pump (8).

The liquid isophoronediurea (8) withdrawn from the thin-film evaporator (C) is fed directly to a fluidized-bed reactor (D). The temperature of said reactor is 380° C. Sand (3.5 kg) was used as the fluidized medium. The diameter of said reactor is 10 cm. The vapors (9) leaving the reactor were rapidly cooled in a flash (E) with toluene (10) in order to separate the resultant isophorone diisocyanate (IPDI, (11)) rapidly from the ammonia. The IPDI yield in this process stage was 90%. The ureas formed during the separation were recycled to the thin-film evaporator (C) (12).

The invention claimed is:

1. A process for the preparation of a di- or polyisocyanate, comprising:
   reacting at least one di- or poly-amine with urea to form a di- or poly-urea and ammonia;
   removing the ammonia formed in the reaction of the at least one di- or polyamine with urea;
   separating off excess urea and minor components formed in the reaction from the formed di- or poly-urea; and
   thermally decomposing the di- or poly-urea from which ammonia, excess urea and minor components have been separated in a disintegrator to form a crude di- or poly-isocyanate and ammonia to obtain vapors containing di- or poly-urea and ammonia;
   and
   cooling the obtained vapors to separate the di- or poly-urea from the ammonia;
   wherein a residence time in the thermal disintegrator for the thermal decomposition is from 0.01 to 20 seconds.

2. The process according to claim 1, further comprising:
   purifying the crude di- or polyisocyanate obtained in at least one distillation; and
   recycling at least part of residues from the purification of the di- or polyisocyanate;
   wherein
   no alcohol is present in the reacting of the at least one organic di- or polyamine with urea and optionally comprises at least one catalyst is present, and
   the separating off of urea and minor components comprises dissolution in water, an alcohol or a solvent having a urea solubility greater than 200 g per liter.

3. The process according to claim 1, wherein the at least one di- or polyamine is at least one selected from the group consisting of 2,4- and 2,6-toluenediamine, 4,4'-, 2,4'- and 2,2'-diaminodiphenylmethane, butanediamine-1,4,2-ethylbutanediamine-1,4, octanediamine-1,8, decanediamine-1,10, dodecanediamine-1,12, cyclohexanediamine-1,4,2-methyl-, 4 methylcyclohexanediamine-1,3,1,3- and 1,4-diaminomethylcyclohexane, 4,4'-di(aminocyclohexyl)methane, 3,8- and 4,9-bis(aminomethyl)-tricyclo[5.2.1.02.6] decane isomer mixtures, 2-methylpentanediamine-1,5,2,2,4- or 2,4,4-trimethylhexanediamine-1,6, hexanediamine-1,6, and 3-aminomethyl-3,5,5-trimethylcyclohexylamine.

4. The process according to claim 2, wherein the separating off the excess urea comprises: dissolving the excess urea out of the reaction mixture with water.

5. The process according to claim 1, wherein the thermal decomposition of the di- or polyurea is carried out in a breakdown reactor selected from the group consisting of tubular ovens, thin-film evaporators, bulk evaporators, Robert evaporators, Herbert evaporators, Caddle-type evaporators, plate reactors, glow-plug evaporators, and fluidized-bed reactors.

6. The process according to claim 1, wherein the breaking down of the di- or polyamine comprises thermally decomposing the di- or polyamine in a fluidized-bed reactor employing a fluidized medium selected from the group consisting of silicon oxide, carbon, and steatite.

7. The process according to claim 2, wherein a water content, alcohol content or water and alcohol content of the di- or poly-urea formed in the separation of excess urea and minor components, is not more than 10% by weight.

8. The process according to claim 2, further comprising: cooling the breakdown product mixture formed in the thermal decomposition for an average cooling time of less than 10 seconds.

9. The process according to claim 8, wherein the cooling comprises a quenching medium.

10. The process according to claim 9, wherein the quenching medium is selected from the group consisting of toluene, benzene, nitrobenzene, anisole, chlorobenzene, ortho- or para-dichlorobenzene, trichlorobenzene, xylene, hexane, diethyl isophthalate (DEIP), aromatic and/or aliphatic hydrocarbon-containing mixtures, having a boiling range of from 60 to 200° C., tetrahydrofuran (THF), and dimethylformamide (DMF).

11. The process according to claim 9, wherein a temperature of the quenching medium is from 0 to 200° C.

* * * * *